United States Patent
Allen, IV et al.

(10) Patent No.: US 10,588,686 B2
(45) Date of Patent: Mar. 17, 2020

(54) SURGICAL INSTRUMENTS WITH STRUCTURES TO PROVIDE ACCESS FOR CLEANING

(71) Applicant: COVIDIEN LP, Mansfield, MA (US)

(72) Inventors: James D. Allen, IV, Broomfield, CO (US); Robert M. Sharp, Boulder, CO (US); Kristel L. Ambrosius, Cary, NC (US); Glenn A. Horner, Boulder, CO (US); Daniel A. Joseph, Golden, CO (US); Peter M. Mueller, Frederick, CO (US); Duane E. Kerr, Loveland, CO (US); Ryan C. Artale, Crested Butte, CO (US)

(73) Assignee: Covidien LP, Mansfield, MA (US)

( * ) Notice: Subject to any disclaimer, the term of this patent is extended or adjusted under 35 U.S.C. 154(b) by 634 days.

(21) Appl. No.: 15/347,041

(22) Filed: Nov. 9, 2016

(65) Prior Publication Data
US 2017/0049506 A1    Feb. 23, 2017

Related U.S. Application Data

(63) Continuation of application No. 13/922,377, filed on Jun. 20, 2013, now Pat. No. 9,510,891.
(Continued)

(51) Int. Cl.
*A61B 18/14*    (2006.01)
*A61B 18/08*    (2006.01)
(Continued)

(52) U.S. Cl.
CPC ........ *A61B 18/1445* (2013.01); *A61B 18/082* (2013.01); *A61B 90/08* (2016.02);
(Continued)

(58) Field of Classification Search
CPC . A61B 18/1445; A61B 18/082; A61B 18/085; A61B 90/08; A61B 2090/0813
(Continued)

(56) References Cited

U.S. PATENT DOCUMENTS

D249,549 S    9/1978  Pike
D263,020 S    2/1982  Rau, III
(Continued)

FOREIGN PATENT DOCUMENTS

CN    101467911 A    7/2009
CN    201299462 Y    9/2009
(Continued)

OTHER PUBLICATIONS

Extended European Search Report dated Jun. 14, 2017, corresponding to European Application No. 13173792.6; 9 pages.
(Continued)

*Primary Examiner* — Thomas A Giuliani
*Assistant Examiner* — Christine A Dedoulis
(74) *Attorney, Agent, or Firm* — Carter, DeLuca & Farrell, LLP

(57) ABSTRACT

A surgical instrument configured to facilitate access to interior components thereof for cleaning and refurbishment purposes includes a housing assembly, an elongated shaft assembly and an end effector. The housing assembly includes an actuator, and the elongated shaft assembly includes an interior control member operatively coupled to the actuator. The elongated shaft assembly also includes outer cover including first and second cover members and a hinge coupling the first and second cover members to one another such that the outer cover may be selectively moved between a closed configuration wherein the interior control member is enclosed within the outer cover and an open configuration wherein the interior control member is
(Continued)

exposed. The end effector is supported at a distal end of the elongated shaft assembly, and is operatively associated with the interior control member.

19 Claims, 5 Drawing Sheets

Related U.S. Application Data

(60) Provisional application No. 61/664,505, filed on Jun. 26, 2012.

(51) Int. Cl.
*A61B 90/00* (2016.01)
*A61B 17/00* (2006.01)
*A61B 18/00* (2006.01)

(52) U.S. Cl.
CPC ............ *A61B 2017/00477* (2013.01); *A61B 2018/00178* (2013.01); *A61B 2018/1455* (2013.01); *A61B 2090/0813* (2016.02)

(58) Field of Classification Search
USPC .......................................................... 606/51
See application file for complete search history.

(56) References Cited

U.S. PATENT DOCUMENTS

| | | | |
|---|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 4,950,273 A | 8/1990 | Briggs |
| D343,453 S | 1/1994 | Noda |
| 5,308,358 A | 5/1994 | Bond et al. |
| D348,930 S | 7/1994 | Olson |
| D349,341 S | 8/1994 | Lichtman et al. |
| 5,336,238 A | 8/1994 | Holmes et al. |
| 5,342,391 A | 8/1994 | Foshee et al. |
| 5,352,235 A | 10/1994 | Koros et al. |
| D354,564 S | 1/1995 | Medema |
| D358,887 S | 5/1995 | Feinberg |
| 5,499,992 A | 3/1996 | Meade et al. |
| 5,507,772 A | 4/1996 | Shutt et al. |
| 5,527,339 A * | 6/1996 | Koscher ................ A61B 17/29 606/205 |
| 5,603,723 A | 2/1997 | Aranyi et al. |
| 5,618,304 A | 4/1997 | Hart et al. |
| D384,413 S | 9/1997 | Zlock et al. |
| H1745 H | 4/1998 | Paraschac |
| D402,028 S | 12/1998 | Grimm et al. |
| 5,851,214 A | 12/1998 | Larsen et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| 6,464,702 B2 | 10/2002 | Schulze et al. |
| D465,281 S | 11/2002 | Lang |
| D466,209 S | 11/2002 | Bon |
| 6,743,185 B2 | 6/2004 | Weber et al. |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| 6,962,588 B2 | 11/2005 | Sauvageau et al. |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,468,041 B2 | 12/2008 | Rhodes et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,758,580 B2 | 7/2010 | Rothstein et al. |
| D621,503 S | 8/2010 | Otten et al. |
| 7,811,282 B2 | 10/2010 | McClurken |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| 8,317,808 B2 | 11/2012 | Levin et al. |
| 8,377,044 B2 | 2/2013 | Coe et al. |
| 8,550,988 B2 | 10/2013 | Pribanic |
| 8,747,401 B2 | 6/2014 | Gonzalez et al. |
| 9,510,891 B2 | 12/2016 | Allen, IV et al. |
| 2005/0085691 A1 | 4/2005 | Nakao |
| 2005/0236459 A1 | 10/2005 | Gresham |
| 2006/0079879 A1 | 4/2006 | Faller et al. |
| 2006/0111723 A1 | 5/2006 | Chapolini et al. |
| 2006/0241532 A1 | 10/2006 | Murakami |
| 2009/0088667 A1 | 4/2009 | Masuda |
| 2011/0319888 A1 | 12/2011 | Mueller et al. |
| 2012/0116363 A1 | 5/2012 | Houser et al. |
| 2013/0138129 A1 * | 5/2013 | Garrison ............ A61B 18/1445 606/170 |

FOREIGN PATENT DOCUMENTS

| | | |
|---|---|---|
| CN | 101574272 A | 11/2009 |
| DE | 2415263 A1 | 10/1975 |
| DE | 2514501 A1 | 10/1976 |
| DE | 2627679 A1 | 1/1977 |
| DE | 3423356 A1 | 1/1986 |
| DE | 3612646 A1 | 4/1987 |
| DE | 3627221 A1 | 2/1988 |
| DE | 8712328 U1 | 2/1988 |
| DE | 4303882 A1 | 8/1994 |
| DE | 4403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 10031773 A1 | 11/2001 |
| DE | 10045375 A1 | 4/2002 |
| DE | 20121161 U1 | 4/2002 |
| DE | 10064623 C1 | 8/2002 |
| DE | 69814283 T2 | 3/2004 |
| DE | 102004026179 A1 | 12/2005 |
| DE | 202007009165 U1 | 8/2007 |
| DE | 202007009317 U1 | 8/2007 |
| DE | 202007009318 U1 | 8/2007 |
| DE | 202007016233 U1 | 1/2008 |
| DE | 102008018406 B3 | 7/2009 |

(56) References Cited

FOREIGN PATENT DOCUMENTS

| | | |
|---|---|---|
| EP | 1159926 A2 | 12/2001 |
| EP | 1281878 A1 | 2/2003 |
| EP | 1836973 A2 | 9/2007 |
| EP | 2111782 A2 | 10/2009 |
| JP | H0061-0501068 A | 9/1984 |
| JP | H055106 A | 1/1993 |
| JP | H0540112 A | 2/1993 |
| JP | H06502328 A | 3/1994 |
| JP | H06121797 A | 5/1994 |
| JP | H06285078 A | 10/1994 |
| JP | H06343644 A | 12/1994 |
| JP | H06511401 A | 12/1994 |
| JP | H07265328 A | 10/1995 |
| JP | H0856955 A | 3/1996 |
| JP | H082-52263 A | 10/1996 |
| JP | H08289895 A | 11/1996 |
| JP | H083-17934 A | 12/1996 |
| JP | H08317936 A | 12/1996 |
| JP | H0910223 A | 1/1997 |
| JP | H09122138 A | 5/1997 |
| JP | H10-24051 A | 1/1998 |
| JP | H10-155798 A | 6/1998 |
| JP | H11-47149 A | 2/1999 |
| JP | H11-47150 A | 2/1999 |
| JP | H11-70124 A | 3/1999 |
| JP | H11-169381 A | 6/1999 |
| JP | H11-192238 A | 7/1999 |
| JP | H11-244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001003400 A | 1/2001 |
| JP | 2001008944 A | 1/2001 |
| JP | 2001029355 A | 2/2001 |
| JP | 2001029356 A | 2/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2009000538 A | 1/2009 |
| JP | 2010000195 A | 1/2010 |
| JP | 2011125195 A | 6/2011 |
| JP | 6030945 B2 | 11/2016 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0239903 A2 | 5/2002 |
| WO | 0245589 A2 | 6/2002 |
| WO | 2006021269 A1 | 3/2006 |
| WO | 05110264 A3 | 4/2006 |
| WO | 2008040483 A1 | 4/2008 |
| WO | 2011018154 A1 | 2/2011 |
| WO | 2011156168 A1 | 12/2011 |

OTHER PUBLICATIONS

U.S. Appl. No. 14/182,967, filed Feb. 18, 2014, Latimer.
U.S. Appl. No. 14/183,090, filed Feb. 18, 2014, Arts.
U.S. Appl. No. 14/188,935, filed Feb. 25, 2014, Reschke.
U.S. Appl. No. 14/196,066, filed Mar. 4, 2014, McCullough.
U.S. Appl. No. 14/204,770, filed Mar. 11, 2014, Dumbauld.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales-Product Literature; Dec. 31, 2000.
Johnson et al. "Evaluation of a Bipolar Electrothermal Vessel Sealing Device in Hemorrhoidectomy" Sales-Product Literature; Jan. 2004.
E. David Crawford "Evaluation of a New Vessel Sealing Device in Urologic Cancer Surgery" Sales-Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales-Product Literature 1999.
LigaSure Vessel Sealing System, the Seal of Confidence in General, Gynecologic, Urologic, and Laparaoscopic Surgery; Sales-Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for be Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.

(56) References Cited

OTHER PUBLICATIONS

Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales-Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales-Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul.-Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales-Product Literature 2000.
Jarrett et al., "Use of the LigaSure Vessel Sealing System for Peri-Hilar Vessels in Laparoscopic Nephrectomy" Sales-Product Literature 2000.
Crouch et al. "A Velocity-Dependent Model for Needle Insertion in Soft Tissue" MICCAI 2005; LNCS 3750 pp. 624-632 Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales-Product Literature 1999.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 13/731,674, filed Dec. 31, 2012, Siebrecht.
U.S. Appl. No. 14/019,031, filed Sep. 5, 2013, Garrison.
U.S. Appl. No. 14/019,094, filed Sep. 5, 2013, Garrison.
U.S. Appl. No. 14/032,486, filed Sep. 20, 2013, Kendrick.
U.S. Appl. No. 14/035,423, filed Sep. 24, 2013, Garrison.
U.S. Appl. No. 14/037,772, filed Sep. 26, 2013, Frushour.
U.S. Appl. No. 14/041,995, filed Sep. 30, 2013, Kendrick.
U.S. Appl. No. 14/042,947, filed Oct. 1, 2013, Craig.
U.S. Appl. No. 14/043,039, filed Oct. 1, 2013, Rusin.
U.S. Appl. No. 14/043,322, filed Oct. 1, 2013, O'Neill.
U.S. Appl. No. 14/047,474, filed Oct. 7, 2013, Mueller.
U.S. Appl. No. 14/050,593, filed Oct. 10, 2013, Plaven.
U.S. Appl. No. 14/052,827, filed Oct. 14, 2013, Nau.
U.S. Appl. No. 14/052,856, filed Oct. 14, 2013, Latimer.
U.S. Appl. No. 14/052,871, filed Oct. 14, 2013, Kappus.
U.S. Appl. No. 14/054,173, filed Oct. 15, 2013, Payne.
U.S. Appl. No. 14/054,573, filed Oct. 15, 2013, Harper.
U.S. Appl. No. 14/064,310, filed Oct. 28, 2013, Reschke.
U.S. Appl. No. 14/065,644, filed Oct. 29, 2013, Reschke.
U.S. Appl. No. 14/080,564, filed Nov. 14, 2013, Lawes.
U.S. Appl. No. 14/080,581, filed Nov. 14, 2013, Kerr.
U.S. Appl. No. 14/083,696, filed Nov. 19, 2013, Horner.
U.S. Appl. No. 14/086,399, filed Nov. 21, 2013, Allen.
U.S. Appl. No. 14/091,505, filed Nov. 27, 2013, Garrison.
U.S. Appl. No. 14/091,521, filed Nov. 27, 2013, Garrison.
U.S. Appl. No. 14/091,532, filed Nov. 27, 2013, Garrison.
U.S. Appl. No. 14/098,953, filed Dec. 6, 2013, Cunningham.
U.S. Appl. No. 14/100,237, filed Dec. 9, 2013, Reschke.
U.S. Appl. No. 14/103,971, filed Dec. 12, 2013, Roy.
U.S. Appl. No. 14/105,374, filed Dec. 13, 2013, Moua.
U.S. Appl. No. 14/109,459, filed Dec. 17, 2013, Hoarau.
U.S. Appl. No. 14/149,343, filed Jan. 7, 2014, Schmaltz.
U.S. Appl. No. 14/152,618, filed Jan. 10, 2014, Artale.
U.S. Appl. No. 14/152,690, filed Jan. 10, 2014, Hart.
U.S. Appl. No. 14/153,346, filed Jan. 13, 2014, Collings.
U.S. Appl. No. 14/162,192, filed Jan. 23, 2014, Garrison.
U.S. Appl. No. 14/164,569, filed Jan. 27, 2014, Heard.
U.S. Appl. No. 14/169,358, filed Jan. 31, 2014, Reschke.
U.S. Appl. No. 14/172,050, filed Feb. 4, 2014, Johnson.
U.S. Appl. No. 14/173,391, filed Feb. 5, 2014, Kharin.
U.S. Appl. No. 14/176,341, filed Feb. 10, 2014, Hart.
U.S. Appl. No. 14/176,684, filed Feb. 10, 2014, Chojin.
U.S. Appl. No. 14/177,812, filed Feb. 11, 2014, Dycus.
U.S. Appl. No. 14/178,540, filed Feb. 12, 2014, Anderson.
U.S. Appl. No. 14/182,894, filed Feb. 18, 2014, Hart.
Chinese Second Office Action and Search Report (with English translation), dated Nov. 30, 2016, corresponding to Chinese Application No. 201310374244.1; 19 total pages.
Chinese Office Action and Search Report (with English Translation), dated Mar. 29, 2016, corresponding to Chinese Application No. 201310374244.1; 21 pages.
Chinese Office Action dated Apr. 2, 2019 (received Apr. 27, 2019), issued in CN Appln. No. 201710699216.

* cited by examiner

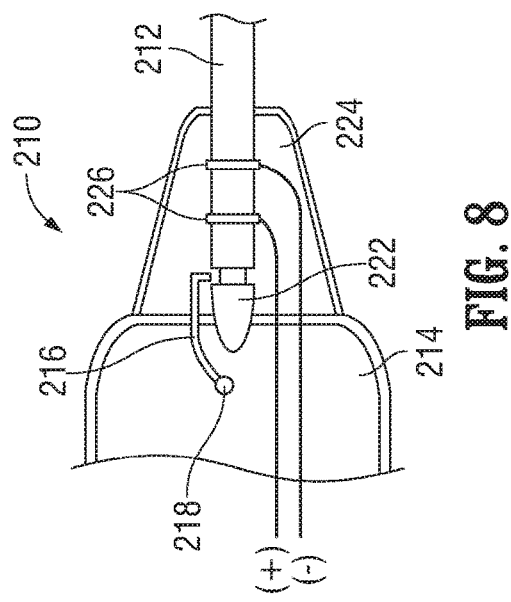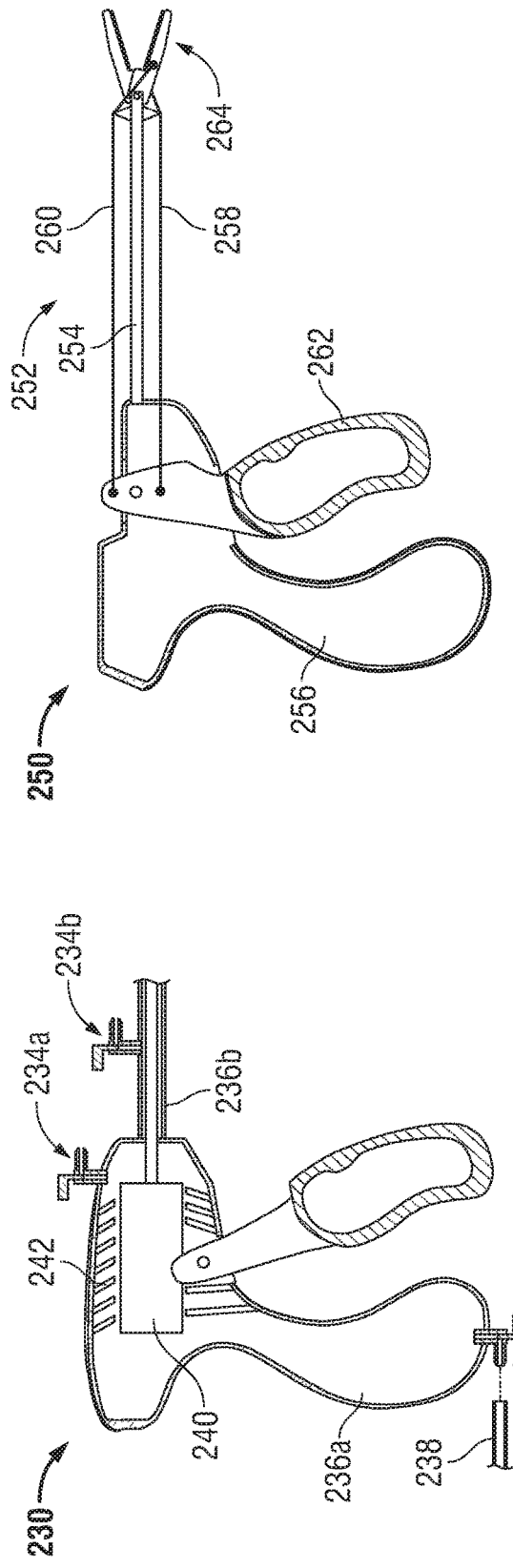

SURGICAL INSTRUMENTS WITH STRUCTURES TO PROVIDE ACCESS FOR CLEANING

CROSS-REFERENCE TO RELATED APPLICATIONS

This application is a continuation application of U.S. patent application Ser. No. 13/922,377, filed on Jun. 20, 2013, which claims the benefit of U.S. Provisional Application No. 61/664,505, filed Jun. 26, 2012, the entire contents of which are incorporated by reference herein.

BACKGROUND

1. Technical Field

The present disclosure relates generally to the field of reposable or reusable surgical instruments. In particular, the disclosure relates to instruments having structures for facilitating cleaning and refurbishment of the instruments for reuse.

2. Background of Related Art

Instruments such as electrosurgical forceps are commonly used in open and endoscopic surgical procedures to coagulate, cauterize and seal tissue. Such forceps typically include a pair of jaws that can be controlled by a surgeon to grasp targeted tissue, such as, e.g., a blood vessel. The jaws may be approximated to apply a mechanical clamping force to the tissue, and are associated with at least one electrode surface to permit the delivery of electrosurgical energy to the tissue. The combination of the mechanical clamping force and the electrosurgical energy has been demonstrated to join adjacent layers of tissue captured between the jaws. When the adjacent layers of tissue include the walls of a blood vessel, sealing the tissue may result in hemostasis. Thereafter, the sealed tissue may be transected by advancing a knife through the jaws. A detailed discussion of the use of an electrosurgical forceps may be found in U.S. Pat. No. 7,255,697 to Dycus et al.

In use, various tissue-contacting components of an electrosurgical forceps tend to become contaminated or degraded. For example, electrodes may become contaminated as portions of the treated tissue adhere to the tissue-contacting surfaces of the electrodes. Also, a knife blade may become dull and less effective in transecting sealed tissue after repeated use, even in a single surgical procedure. In order to provide clean electrodes and a sharp knife for a particular surgical procedure, a brand new instrument is often used. Once the procedure is complete, the used instrument is discarded.

Instruments that are reposable, or reusable for multiple procedures, reduce the instrumentation costs per procedure. Providing a reusable electrosurgical forceps, however, presents various challenges. For example, the complexity of an electrosurgical forceps tends to result in fairly labor intensive cleaning procedures to prepare the forceps for subsequent use. Improper cleaning may result in dangerous contamination being introduced into the surgical site. Also, some reusable forceps have removable and replaceable components that provide clean surfaces for each use. Many of these instruments require arduous disassembly and reassembly procedures that require extensive training, and may discourage use of the instrument.

SUMMARY

The present disclosure describes a surgical instrument for treating tissue. The surgical instrument includes a housing assembly having an actuator and an elongated shaft assembly defining a longitudinal axis and extending from the housing assembly. The elongated shaft assembly includes an interior control member operatively coupled to the actuator, and an outer cover including first and second cover members. A hinge couples the first and second cover members to one another such that the outer cover may be selectively moved between a closed configuration wherein the interior control member is enclosed within the outer cover and an open configuration wherein the interior control member is exposed to an exterior of the instrument. The instrument also includes an end effector supported at a distal end of the elongated shaft assembly that is operatively associated with the interior control member.

The hinge may extend along a longitudinal seam defined between the first and second cover members, and the end effector may be releasably supported at the distal end of the elongated shaft assembly. The end effector may move unencumbered in a lateral direction when the outer cover is in the open configuration and movement of the end effector may be encumbered by the outer cover when the outer cover is in the closed configuration. The elongated shaft assembly may also include a latch for selectively maintaining the outer cover in the closed configuration.

The interior control member may be a reciprocating member longitudinally movable in response to manipulation of the actuator. The end effector may include a pair of jaw members movable from an open configuration wherein the jaw members are substantially spaced relative to one another to a closed configuration wherein the jaw members are closer together in response to longitudinal motion of the control member.

The hinge may also be defined along a distal edge of the first and second cover members, and the elongated shaft assembly may include a structural support extending between the housing assembly and the end effector. The structural support maintains a longitudinal distance between the housing assembly and the end effector and is disposed such that it is enclosed within the outer cover when the outer cover is in the closed configuration.

According to another aspect of the disclosure a surgical instrument includes a housing assembly having an actuator, and an elongated shaft assembly defining a longitudinal axis and extending from the housing assembly. The elongated shaft assembly includes an interior control member operatively coupled to the actuator. An end effector is supported at a distal end of the elongated shaft assembly and is operatively associated with the interior control member. A hinge is operable to selectively provide access to the interior control member for cleaning and to selectively restrict access to the interior control member during operation of the instrument.

The elongated shaft assembly may include first and second cover members, and the hinge may be disposed between the first and second cover members of the shaft assembly. Alternatively or additionally, the housing assembly may include first and second housing members, and the hinge may be disposed between the first and second housing members of the housing assembly. At least one of the first and second housing members may include a conformable material around a periphery thereof for forming a hermetic seal when engaged with the other of the first and second housing members. The hinge may be positioned to permit the first and second housing members to open along a plane substantially normal to the elongated shaft assembly. The interior control member may include a connector at a proximal end thereof for engaging a proximal drive member within the housing, and the proximal drive member may be operatively associated with the actuator. The housing assembly may also include a latch for maintaining the first and second housing members in a closed configuration and for maintaining engagement of the connector with the proximal drive member.

The surgical instrument may also include a cable extending from the housing assembly. The cable may be connectable to a source of electrosurgical energy, and the connector may include electrical contacts thereon for receiving electrosurgical energy from the cable.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIG. 8 is a partial schematic view of a connection mechanism for facilitating releasable connection of a shaft assembly to a housing of an instrument in accordance with an alternate embodiment of the present disclosure;

FIG. 9 is a schematic view of an endoscopic surgical instrument having a housing with fluid ports to permit circulation of a cleaning solution through an interior of the housing; and FIG. 10 is a schematic view of an endoscopic surgical instrument having a skeleton-like external shaft including exposed reciprocating members.

DETAILED DESCRIPTION

The present disclosure is directed to instruments having structures for facilitating cleaning and refurbishment of the instruments for reuse. Many of the instruments described herein include structures that provide access to interior components, which may become contaminated during a surgical procedure.

Figure 1:
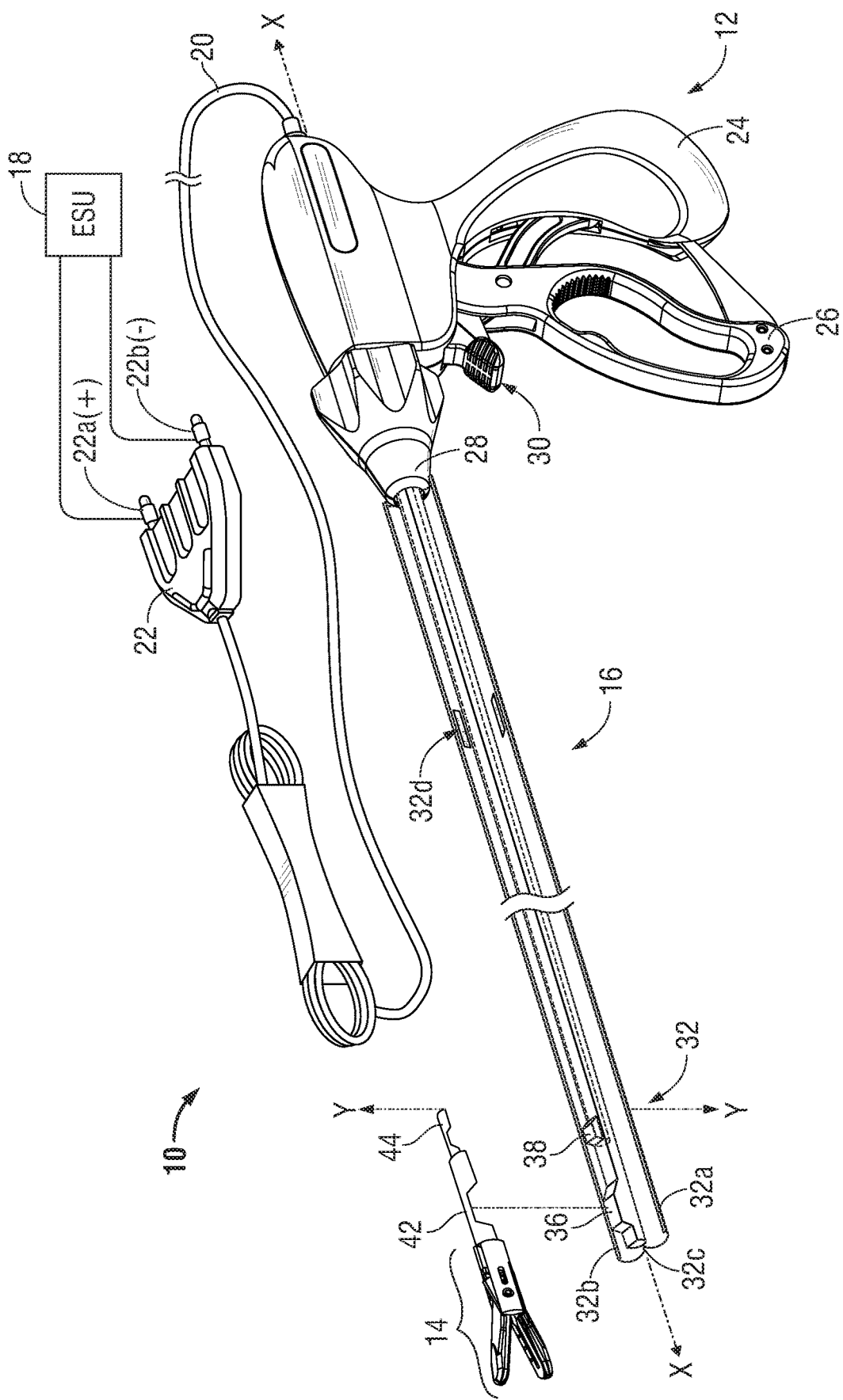
FIG. 1 is a perspective view of an endoscopic surgical instrument having a hinged shaft assembly in accordance with an embodiment of the present disclosure.

Referring initially to FIG. 1, an embodiment of an electrosurgical instrument 10 is depicted. The instrument 10 includes a housing or handle assembly 12 for remotely controlling an end effector 14 through an elongated shaft assembly 16. Although this configuration is typically associated with instruments for use in laparoscopic or endoscopic surgical procedures, various aspects of the present disclosure may be practiced with traditional open instruments, and in connection with endoluminal procedures as well.

The instrument 10 is coupled to a source of electrosurgical energy, e.g., an electrosurgical generator 18. Generator 18 may include devices such as the LIGASURE® Vessel Sealing Generator and the Force Triad® Generator as sold by Covidien. A cable 20 extends between the handle assembly 12 and the generator 18, and includes a connector 22 for coupling the instrument 10 to the external generator 18. In other embodiments (not shown) a battery powered instrument may be provided in which a generator and connector may be internal or integral with the instrument 10. The connector 22 includes two prong members 22a and 22b that are dimensioned to physically and electrically connect the instrument 10 to opposite terminals, e.g., positive or active (+) and negative or return (−) terminals associated with the generator 18. Thus, bipolar energy may be provided through the instrument 10. Alternatively, the instrument 10 may be configured for delivering monopolar energy to the tissue. In a monopolar configuration, the instrument 10 delivers electrosurgical energy from an active terminal, e.g. (+), while a return pad (not shown) is placed generally beneath a patient and provides a return path to the opposite terminal, e.g. (−), of the generator 18.

To control the end effector 14, the handle assembly 12 includes a stationary handle 24 and movable handle 26. The movable handle 26 may be separated and approximated relative to the stationary handle 24 to respectively open and close the end effector 14. A rotation knob 28 is provided on the handle assembly 12 to permit rotation of the elongated shaft assembly 16 and the end effector 14 about a longitudinal axis X-X defined by the elongated shaft assembly 16. A trigger 30 is also disposed on the handle assembly 12, and is operable to extend and retract a knife 204 (see, e.g., FIG. 7) through the end effector 14. A footswitch (not shown) may be provided to initiate and terminate the delivery of electrosurgical energy to the end effector 14.

The elongated shaft assembly 16 includes hinged outer cover 32 with a lower member 32a and an upper member 32b. The lower member 32a is fixed to the rotation knob 28, and the upper member 32b is pivotally connected to the lower member 32a about a longitudinal hinge 32c that is parallel to the longitudinal axis X-X. The outer cover 32 is thus movable between a closed configuration wherein the outer cover 32 exhibits a generally circular cross section, and an open configuration as depicted. The outer cover 32 includes a latch 32d, which maintains the cover 32 in the closed configuration during use of the instrument 10. When the cover 32 is in the closed configuration, a hermetic seal is established between the lower and upper members 32a, 32b of the outer cover 32. One or both of the lower and upper members 32a, 32b may include a conformable material (see, e.g., FIG. 4) along an edge or periphery thereof such that a hermetic seal is formed when the lower and upper members 32a, 32b engage one another.

Extending through the outer cover 32 is a pair of control members or reciprocating members 36 and 38. Reciprocating member 36 is operatively coupled to the moveable handle 26 and reciprocating member 38 is operatively coupled to the trigger 30 such that respective operation of the moveable handle 26 and the trigger 30 induces longitudinal motion of the reciprocating members 36, 38 through the outer cover 32. A distal end of the reciprocating member 36 includes an undulating trapezoidal profile to permit the reciprocating member 36 to interlock with a correspondingly shaped proximal end of a drive member 42 extending from the end effector 14 to transfer longitudinal motion thereto. Similarly, a distal end of the reciprocating member 38 includes an undulating trapezoidal profile to permit the reciprocating member 38 to interlock with a correspondingly shaped proximal end of a drive member 44 extending from the end effector 14. The drive member 42 is operable to move the end effector 14 between the open configuration depicted and a closed configuration (see FIG. 9). The drive member 44 is operable to advance a knife through the end effector 14.

In use, a clinician or an operator may operatively connect the end effector 14 to the movable handle 26 and trigger 30 by approximating the end effector 14 with the shaft assembly 16 in a lateral direction along an axis Y-Y that is transverse to the longitudinal axis X-X to engage the reciprocating member 36 with the drive member 42 and to engage the reciprocating member 38 with the drive member 44. Electrical connectivity may also be established between the end effector 14 and the handle assembly 12 through electrical connectors (not shown). Closing and latching the outer cover 32 will maintain engagement of the reciprocating members 36, 38 with the drive members 42, 44 since the upper member 32*b* of the outer cover 32 interferes with the lateral motion of the end effector 14 when the cover 32 is in the closed configuration. The instrument 10 may then be used in a surgical procedure, which may tend to contaminate interior components such as the reciprocating members 36 and 38. After the procedure, the outer cover 32 may be unlatched and opened to release the end effector 14. In the open configuration the reciprocating members 36, 38 are exposed, and may be readily scrubbed, washed and/or sterilized. The end effector 14 may be sterilized or replaced to ready the instrument 10 for subsequent use.

Figure 2:
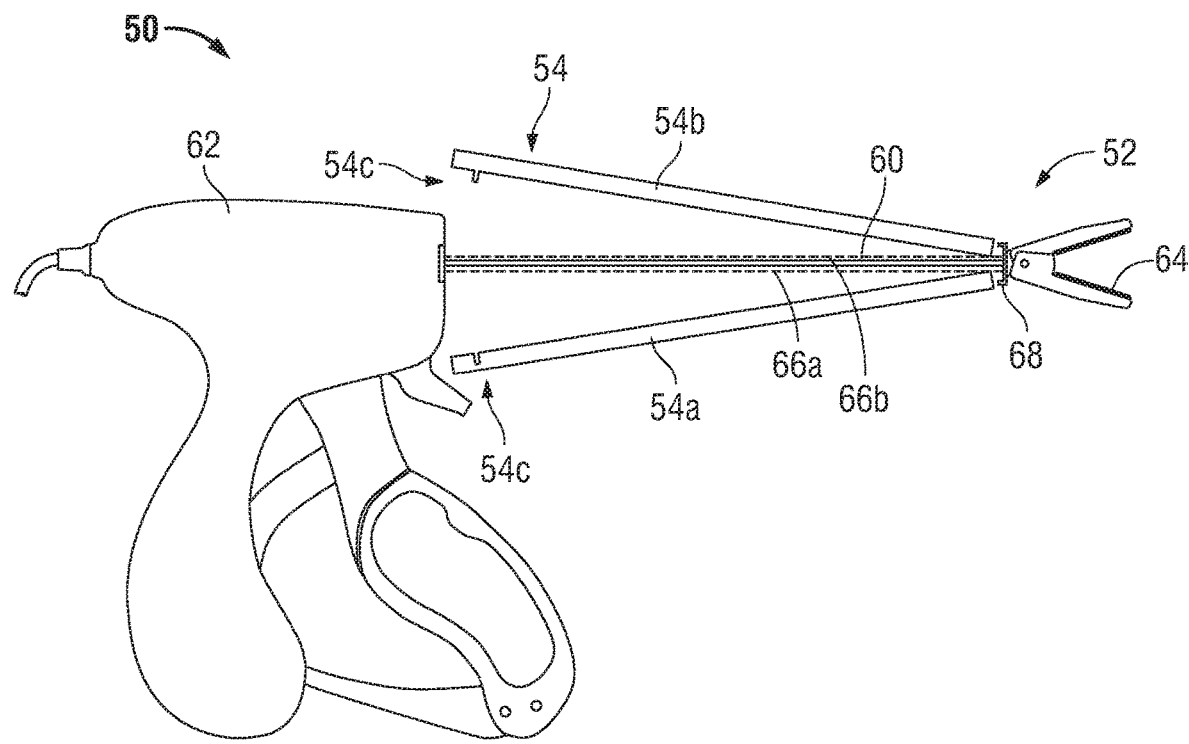
FIG. 2 is a side view of an endoscopic surgical instrument having a clamshell shaft assembly in accordance with an alternate embodiment of the present disclosure.

Referring now to FIG. 2, an instrument 50 includes an elongated shaft assembly 52 that employs an alternate mechanism for providing access to the interior shaft components. The elongated shaft assembly 52 includes a clamshell outer cover 54 including a lower clamshell member 54*a* and an upper clamshell member 54*b*. The outer cover 54 includes a snap fit inter-engaging connector 54*c* for selectively coupling the upper and lower clamshell members 54*a*, 54*b* to one another. The elongated shaft assembly 52 includes a structural support 60 extending between housing 62 and end effector 64. The structural support 60 maintains the end effector 64 at a fixed longitudinal distance from the housing 62 as reciprocating members 66*a* and 66*b* (depicted schematically in phantom) move to activate the end effector 64 and knife (not shown). An electrical signal may be transmitted through the structural support 60 to provide the end effector 64 with electrosurgical energy.

The electrical signal may be transmitted via a monopolar, bipolar, or multi-polar arrangement associated with the instrument 50. In the case of monopolar transmission, the electrical signal passes through the end effector 64 via one or more electrodes (not shown in detail) disposed thereon, through the tissue, and to a return electrode such as a return pad (not shown). In the instance of a bipolar arrangement, the electrical signal may pass from a first electrode (not shown in detail) disposed in the end effector 64 through the tissue and into a second electrode (not shown in detail) disposed on another portion of the end effector 64. A multi-polar instrument may combine three or more electrodes placed on or in electrical proximity to end effector 64 such that the electrical path of the electrical signal may be modified or selected during a procedure.

The structural support 60 also includes a stop 68 at a distal end thereof. The stop 68 receives distal ends of the clamshell members 54*a*, 54*b* and facilitates pivoting of the clamshell members 54*a*, 54*b* toward one another to close the outer cover 54. Thus, the stop 68 serves as a hinge defined at a distal edge of the clamshell members 54*a*, 54*b*.

Instrument 50 may further include a knife assembly (not shown in FIG. 2) disposed within clamshell members 54*a*, 54*b* and configured to sever tissue held by end effector 64. The elongated shaft assembly 52, the end effector 64, structural support 60, reciprocating members 66*a*, 66*b*, and or clamshell member 54*a*, 54*b* may also be configured to rotate relative to housing 62.

In use, the outer cover 54 may be closed to protect the structural support 60 and the reciprocating members 66*a*, 66*b* during a surgical procedure. The snap fit connector 54*c* may then be disengaged to open the outer cover 54 and expose the interior components 60, 66*a*, 66*b* to facilitate cleaning of the instrument 50.

Figure 3:
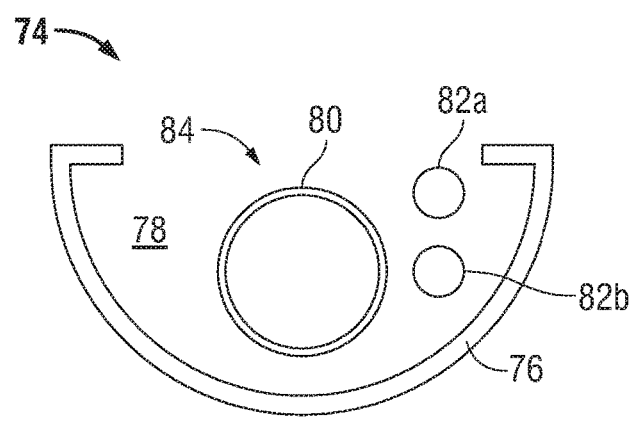
FIG. 3 is a cross-sectional view of an open, u-shaped shaft assembly in accordance with an alternate embodiment of the present disclosure.

Referring now to FIG. 3, an elongated shaft assembly 74 includes an elongated, u-shaped structural support 76. The structural support 76 defines a longitudinal channel 78 in which a reciprocating member 80 and a pair of electrical wires 82*a* and 82*b* extend. The structural support 76 provides protection for the reciprocating member 80 and the wires 82*a*, 82*b*, and provides an open side 84 to provide access to these interior components 80 and 82*a*, 82*b* for cleaning. This open structure may reduce the need for disassembly of the shaft assembly 74 for cleaning, and may also facilitate assembly of the shaft assembly 74 during manufacturing and/or refurbishment of the shaft assembly 74. While not specifically shown in FIG. 3, other devices may also be included within support 76 such as, but not limited to, insufflation tubing, suction tubing, and a knife assembly disposed within the reciprocating member 80 or in any other suitable manner to sever tissue held by an end effector (not shown in FIG. 3). Also, while a pair of wires 82*a* and 82*b* are shown, there may be more or less wires and the wires may be used to transmit an electrical signal in a monopolar, bipolar, or multi-polar fashion. For example, in a monopolar scenario, wires 82*a* and 82*b* transmit electrical current to one or more electrodes on an end effector (not shown in FIG. 3), which travels through tissue and into a return electrode such as an external return pad.

Figure 4:
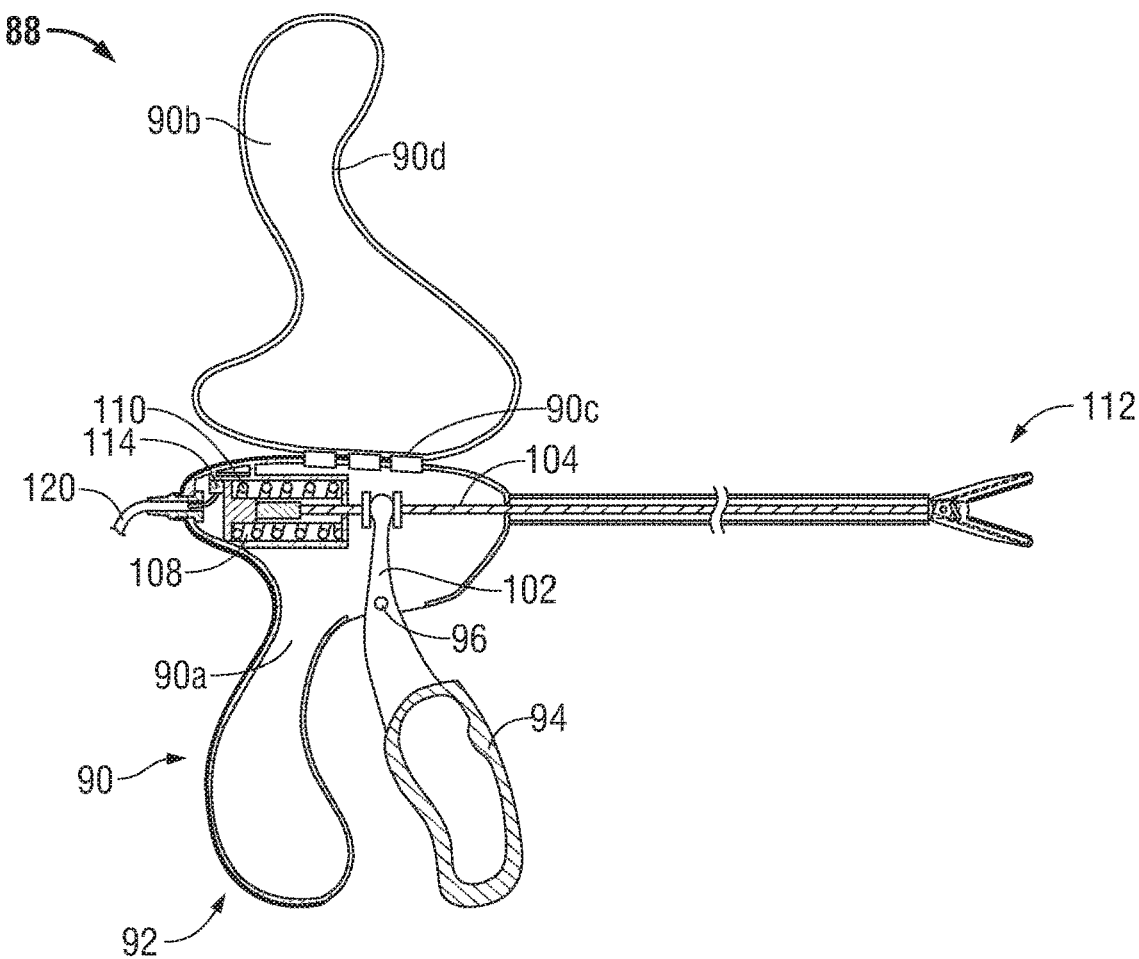
FIG. 4 is a side view of an endoscopic surgical instrument having a hinged housing assembly in accordance with an alternate embodiment of the present disclosure.

Referring now to FIG. 4, an instrument 88 includes a hinged outer cover 90. The outer cover 90 includes a lower housing member 90*a* and an upper housing member 90*b* coupled to one another by a hinge 90*c*. The outer cover 90 may be may be closed to form a stationary handle 92 of the instrument 88, and opened (as depicted) to provide access to an interior of the instrument 88 for cleaning thereof. A band 90*d* of an elastomeric or other conformable material is provided about a periphery of the upper housing member 90*b* to engage a periphery of the lower housing member 90*a* when the outer cover 90 is closed. Thus, the outer cover 90 forms a hermetic seal when closed to discourage the passage of contaminants into the interior of the outer cover 90. The outer cover 90 may be constructed of metal or other heavy-duty materials such that the outer cover 90 may withstand the rigors of multiple surgical uses and refurbishment cycles.

The lower housing member 90 a pivotally supports a movable handle 94 about a pivot point 96. A lever member 102 extends from the movable handle 94 and engages a reciprocating member 104 for imparting longitudinal motion thereto upon pivotal movement of the movable handle 94. A chamber 108 defined at a proximal end of the reciprocating member 104 includes a spring 110 for imparting a biasing force to the reciprocating member 104 to maintain the movable handle 94 in a separated position relative to the stationary handle 92, (and thus, maintain an end effector 112 in an open configuration). The chamber 108 also provides an electrical connector 114 for coupling to electrosurgical cable 120. The chamber 108 may be filled with an epoxy or another protective substance to protect these interior components 110, 114 from contamination. Thus, these components (i.e., spring 110 and electrical connector 114) which may have intricate external geometries and may present difficulty in cleaning, may not require direct cleaning to prepare the instrument 88 for subsequent use. The exterior surfaces of the epoxy may be cleaned, or these components 110, 114 may simply be replaced.

Instrument 88 may further include a knife assembly (not shown in FIG. 4) configured to sever tissue held by end effector 112. Similar to the above disclosed embodiments, the elongated shaft assembly, the end effector 112, structural support 60, and/or reciprocating member 104, may be configured to rotate relative to cover 90. Instrument 88 may also be configured for monopolar, bipolar, or multi-polar use.

Figure 5:
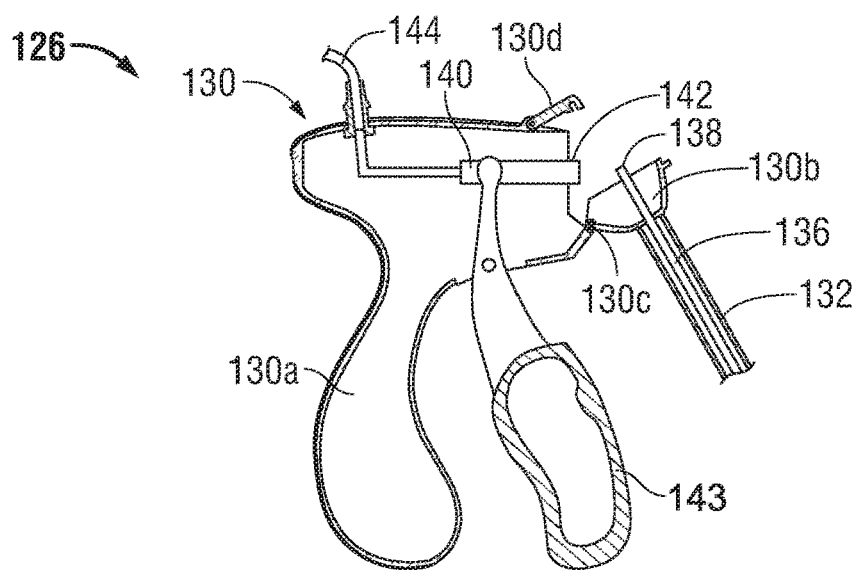
FIG. 5 is a side view of an endoscopic surgical instrument having a hinged housing assembly and a replaceable shaft assembly in accordance with an alternate embodiment of the present disclosure.

Referring now to FIG. 5, an instrument 126 includes a hinged outer cover 130. The outer cover 130 includes a proximal housing member 130a and a distal housing member 130b coupled to one another by a hinge 130c. A latch 130d is provided to allow the outer cover 130 to be maintained in a closed configuration (not shown). The hinge 130c is positioned to permit the hinged outer cover 130 to open along a plane substantially normal to an elongated shaft assembly 132. This arrangement allows the elongated shaft assembly 132 to pivot into alignment with drive member 140.

The elongated shaft assembly 132 is supported by the distal housing member 130b and includes at least one reciprocating member 136 and a connector 138 at a proximal end thereof. The proximal housing member 130a supports a proximal drive member 140 that is longitudinally movable in response to pivotal movement of a movable handle 143. The proximal drive member 140 includes a connector 142 at a distal end thereof for engaging the connector 138 of the reciprocating member 136 when the outer cover 130 is moved to the closed configuration. The engagement of the connectors 138, 142 permit longitudinal motion to be transmitted between the reciprocating member 136 and the proximal drive member 140. The connectors 138, 142 may also include electrical terminals (not shown) that permit an electrosurgical current to be transmitted from electrosurgical cable 144 supported on the proximal housing member 130a to the elongated shaft 130b supported by the distal housing member 130b. The latch 130d maintains the engagement of the connectors 138, 142 as well as maintaining the outer cover 130 in the closed configuration.

Instrument 126 may further include a knife assembly (not shown in FIG. 5) configured to sever tissue held by an end effector (not shown in FIG. 5). Similar to the above disclosed embodiments, the elongated shaft assembly 132, the end effector (not shown in FIG. 5), and/or reciprocating member 136, may be configured to rotate relative to proximal housing member 130a and/or distal housing member 130b. Instrument 126 may also be configured for monopolar, bipolar, or multi-polar use.

In use, the instrument 126 may be used for a surgical procedure with the outer cover 130 in the closed position. Thereafter, to refurbish the instrument 126, the outer cover 130 may be opened to provide access to the elongated shaft assembly 132. The reciprocating member 136, or the entire elongated shaft assembly may be removed from the distal housing member 130b from either an exterior distal side thereof or a proximal interior side thereof. The elongated shaft assembly 132 may then be readily cleaned and replaced.

Figure 6A:
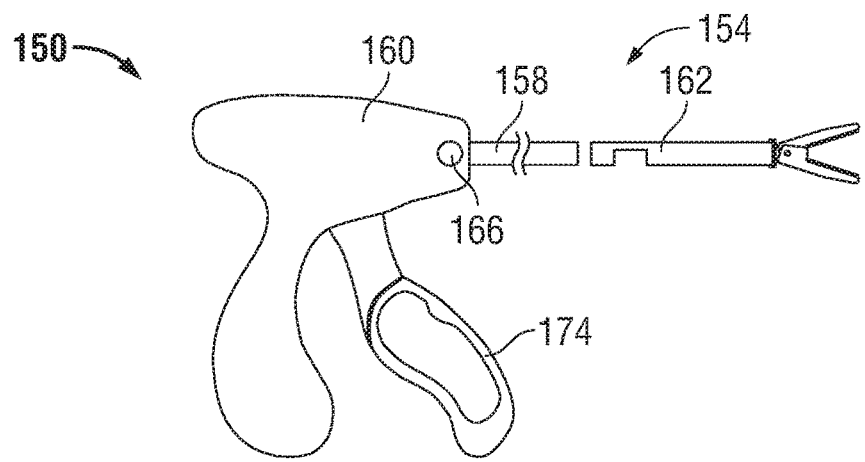
FIG. 6A is a schematic view of an endoscopic surgical instrument having releasable reciprocating members separable from a housing of the instrument in accordance with an alternate embodiment of the present disclosure.
Figure 6B:
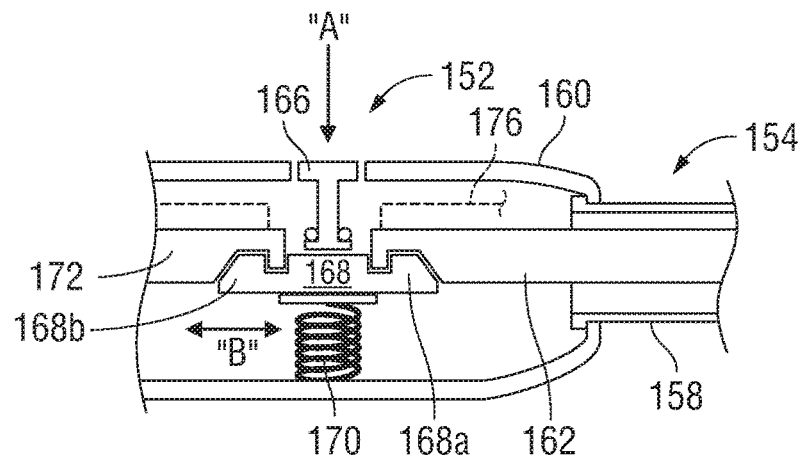
FIG. 6B is a partial, schematic view of a release mechanism for facilitating releasable connection of the reciprocating members of FIG. 6A to the housing of the instrument.

Referring now to FIGS. 6A and 6B, an instrument 150 includes a push button release mechanism 152 for selectively releasing interior components of an elongated shaft assembly 154. The elongated shaft assembly 154 includes an outer shaft member 158 extending from a housing 160, and at least one reciprocating member 162 extending through the outer shaft member 158. Similar to the above disclosed embodiments, the elongated shaft assembly 154, the end effector, and/or reciprocating member 162, may be configured to rotate relative to housing 160. Instrument 150 may also be configured for monopolar, bipolar, or multi-polar use.

The release mechanism 152 permits the reciprocating member 162 to selectively release from engagement with the outer shaft member 158 by depressing push button 166. Pushbutton 166, which is movable relative to the housing in the lateral direction of arrow "A", engages a sled 168, which is biased in a direction opposite arrow "A" by a biasing member such as spring 170. The sled 168 includes opposed hooked ends 168a and 168b that allow the sled 168 to engage the reciprocating member 162 and a proximal drive member 172. The proximal drive member 172 may be operatively coupled to movable handle 174 (see FIG. 6A) to allow longitudinal motion thereto, e.g., in the direction of arrow "B", in response to pivotal motion of the handle 174. The spring 170 normally maintains the engagement of the sled 168 with the reciprocating member 162 and a proximal drive member 172. The sled 168 is movable in the longitudinal direction of arrow "B" such that longitudinal motion may be transmitted between the reciprocating member 162 and the proximal drive member 172.

When the pushbutton 166 is depressed against the bias of the spring 170, the sled 168 is induced to move in the direction of arrow "A" to disengage the reciprocating member 162 and a proximal drive member 172. The reciprocating member 162 may then be removed for cleaning or replacement. When the pushbutton 166 is released, the sled 168 re-engages the proximal drive member 172. To re-connect the reciprocating member 162 to the sled 168, the reciprocating member 162 may be approximated with the sled 168 in the longitudinal direction of arrow "B." Sloped sides of the hooked end 168a of the sled 168 provide a lead-in to facilitate re-connection of the reciprocating member 162.

The release mechanism 152 may accommodate additional reciprocating members e.g., 176. The sled 168 may be arranged to accept multiple reciprocating members 172, 176 arranged in parallel. A knife assembly (not shown in FIGS. 6A and 6B) may also be slidably disposed within reciprocating member 162 configured to sever tissue held by the end effector. The knife assembly (not shown in FIGS. 6A and 6B) may be configured to release via release mechanism 152 similar to reciprocating member 162 or via a separate release mechanism (not shown).

Figure 7:
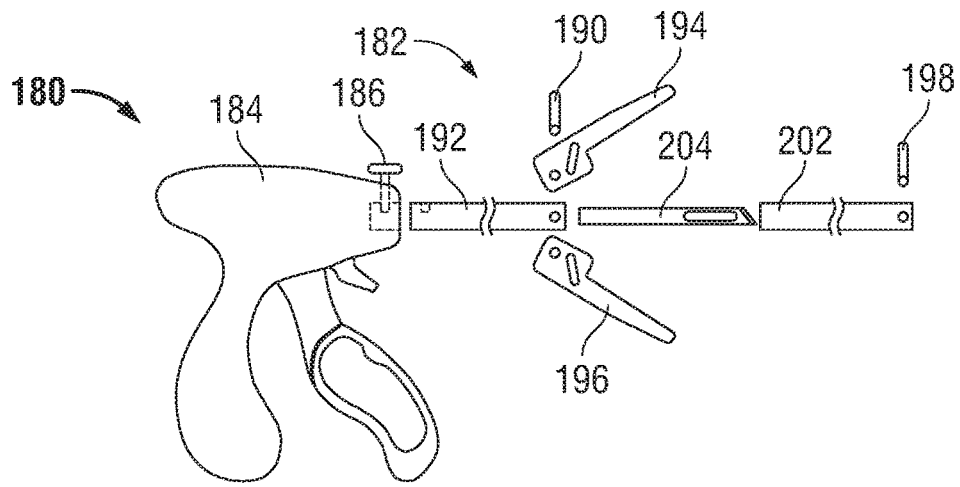
FIG. 7 is a schematic view of an endoscopic surgical instrument having a removable and disassemblable shaft assembly in accordance with an alternate embodiment of the present disclosure.

Referring now to FIG. 7, instrument 180 includes a shaft assembly 182 that is selectively releasable from a housing 184 by a latch 186. Once released from the housing 184, the shaft assembly 182 may be readily disassembled into its constituent parts. For example, a pivot pin 190 may be removed from an outer shaft member 192 and jaw members 194, 196, and a cam pin 198 may be removed from a reciprocating drive tube 202 and a knife 204 to disassemble the shaft assembly 182. Disassembly of the shaft assembly 182 permits the exterior surfaces of each of the constituent parts to be cleaned and/or evaluated for need of replacement. The pivot pin 190 and cam pin 198 may then be reassembled to establish operation of the jaw members 194, 196 as described for example in U.S. Pat. No. 7,255,697 to Dycus et al. Similar to the above disclosed embodiments, the elongated shaft assembly 182 and/or the jaw members 194, 196 may be configured to rotate relative to housing 184. Instrument 180 may also be configured for monopolar, bipolar, or multi-polar use.

Referring now to FIG. 8, a connection mechanism 210 is depicted for selectively securing a removable shaft assembly 212 to an instrument housing 214. The mechanism 210 includes a cam latch 216 that pivots about an axis 218 as a tapered proximal end 222 of the shaft assembly 212 is longitudinally approximated therewith. The cam latch 216 secures the shaft assembly 212 in the housing 214 while permitting rotational motion of the shaft assembly 212 in response to rotation of a rotation knob 224. Round electrical contacts 226 on the shaft assembly 212 permit electrical connectivity to be maintained between the shaft assembly 212 and the housing 214 as the shaft assembly 212 rotates. Connection mechanism 210 may be further configured for use with a knife assembly (not shown in FIG. 8) configured to sever tissue held by an end effector (not shown in FIG. 8). Connection mechanism 210 may be further configured to allow for monopolar, bipolar, or multi-polar use.

Referring now to FIG. 9, instrument 230 includes fluid ports 232 and 234a to permit circulation of a cleaning solution through a housing 236a. The fluid ports 232, 234a are configured to receive a fluid conduit, e.g., conduit 238, and may include a valve for selective opening and closing of the fluid ports 232, 234a. When the ports 232, 234a are closed, the housing 236a may be substantially hermetically sealed. When the ports 232, 234a are opened, a cleaning solution or sterilization fluid delivered under pressure to fluid port 232, may be circulated through the housing 236a past interior components, depicted schematically as 240, and withdrawn from the port 234a. Interior components 240 may include reciprocating members, electrical components, and/or connection mechanisms, etc. for facilitating operation of the instrument 230. The housing 236 may include fins 242 or other obstacles therein that direct a circulating cleaning solution toward the interior components 240.

The port 234a is disposed on the housing 236a. An additional or alternative port 234b may also be disposed on a shaft member 236b, which extends from the housing 236a. The port 234b may be positioned at any location along the shaft member 236b including proximal and distal ends of the shaft member 236b.

Referring now to FIG. 10, an instrument 250 includes a skeleton shaft 252. The shaft 252 includes a structural support 254 extending from a stationary handle 256, and a pair of reciprocating members 258, 260 coupled to a movable handle 262 for actuating an end effector 264. The reciprocating members 258, 260 may be constructed of wires or small rods, and are exposed to an exterior of the instrument 250. Thus, the skeleton shaft 252 represents mechanism with relatively low complexity that may be readily cleaned without any disassembly of the instrument 250.

The various embodiments disclosed herein may also be configured to work with robotic surgical systems and what is commonly referred to as "Telesurgery". Such systems employ various robotic elements to assist the surgeon in the operating room and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments as disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller, or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Although the foregoing disclosure has been described in some detail by way of illustration and example, for purposes of clarity or understanding, it will be obvious that certain changes and modifications may be practiced within the scope of the appended claims.

What is claimed is:

1. A surgical instrument, comprising:
   a housing;
   a drive member movably disposed within the housing;
   an outer shaft defining a longitudinal axis and having a proximal portion configured to couple to the housing;
   a reciprocating member configured to reciprocate along the longitudinal axis defined by the outer shaft; and
   a release mechanism operably coupled to the housing and including a sled detachably coupled between the drive member and the reciprocating member, the sled configured to move along the longitudinal axis and transmit longitudinal motion between the reciprocating member and the drive member, wherein the release mechanism is configured to releasably interconnect the drive member and the reciprocating member via movement of the sled.

2. The surgical instrument according to claim 1, wherein the sled has a proximal portion configured to releasably couple to the drive member and a distal portion configured to releasably couple to a proximal portion of the reciprocating member.

3. The surgical instrument according to claim 2, wherein each of the proximal and distal portions of the sled has a hooked configuration to complimentarily engage the respective drive member and the proximal portion of the reciprocating member.

4. The surgical instrument according to claim 2, wherein the distal portion of the sled defines a tapered surface configured to contact the proximal portion of the reciprocating member upon longitudinal insertion of the reciprocating member into the housing.

5. The surgical instrument according to claim 2, wherein the sled is movable between a first position, in which the sled is aligned with the drive member and the reciprocating member, and a second position, in which the sled is out of alignment with the drive member and the reciprocating member.

6. The surgical instrument according to claim 5, wherein the sled moves in a direction perpendicular to the longitudinal axis as the sled moves between the first and second positions.

7. The surgical instrument according to claim 5, wherein the release mechanism further includes a biasing member configured to bias the sled toward the first position.

8. The surgical instrument according to claim 7, wherein the sled is suspended within a cavity defined in the housing by the biasing member.

9. The surgical instrument according to claim 7, wherein the sled is axially movable relative to the biasing member.

10. The surgical instrument according to claim 7, wherein the biasing member is compressed as the sled moves from the first position toward the second position.

11. The surgical instrument according to claim 7, wherein the release mechanism further includes a button associated with the sled and accessible via an access hole defined in the housing, the sled being slidable relative to the button.

12. The surgical instrument according to claim 11, wherein the sled moves from the first position to the second position in response to movement of the button in a direction perpendicular to the longitudinal axis of the outer shaft.

13. The surgical instrument according to claim 11, wherein the sled is disposed between the biasing member and the button.

14. The surgical instrument according to claim 1, further comprising an end effector supported at a distal portion of the outer shaft and operatively associated with a distal portion of the reciprocating member such that axial movement of the reciprocating member actuates a function of the end effector.

15. A method of disassembling a surgical instrument, comprising:

moving a button of a release mechanism relative to a housing of the surgical instrument along a transverse axis to initiate movement of a sled of the release mechanism out of engagement with a drive member to detach the drive member from a reciprocating member, the drive member disposed within the housing and the reciprocating member extending distally from the housing, wherein the sled is configured to move along a longitudinal axis defined by the drive member and transmit longitudinal motion between the reciprocating member and the drive member; and removing the reciprocating member from the housing.

16. The method according to claim 15, further comprising one of:

cleaning the reciprocating member after the removal thereof; or replacing the reciprocating member with a clean replacement reciprocating member after the reciprocating member is removed from the housing.

17. The method according to claim 15, further comprising:

moving a clean reciprocating member into the housing along a longitudinal axis defined by the clean reciprocating member;

engaging a proximal portion of the clean reciprocating member with a distal portion of the sled to move the sled from a first position, in which the sled is aligned with the clean reciprocating member, to a second position, in which the sled is out of alignment with the clean reciprocating member; and moving the sled from the second position to the first position to form a connection between the proximal portion of the clean reciprocating member and the distal portion of the sled.

18. The method according to claim 17, wherein the sled is moved from the second position to the first position via a biasing member that supports the sled thereon.

19. The method according to claim 15, wherein moving the sled relative to the housing disengages a proximal portion of the sled from the drive member disposed within the housing.

* * * * *